(12) United States Patent
Yan et al.

(10) Patent No.: US 11,033,562 B2
(45) Date of Patent: Jun. 15, 2021

(54) CARBOHYDRATE DERIVATIVES USED FOR SURFACE MODIFICATION OF IMMUNE CELLS, USE THEREOF AND METHOD THEREOF

(71) Applicant: Xiamen Nuokangde Biological Technology Co., Ltd., Fujian (CN)

(72) Inventors: Xu Yan, Fujian (CN); Zhu Li, Fujian (CN)

(73) Assignee: Xiamen Nuokangde Biological Technology Co., Ltd., Siming District (CN)

( * ) Notice: Subject to any disclaimer, the term of this patent is extended or adjusted under 35 U.S.C. 154(b) by 0 days.

(21) Appl. No.: 16/791,079

(22) Filed: Feb. 14, 2020

(65) Prior Publication Data

US 2020/0197426 A1 Jun. 25, 2020

Related U.S. Application Data

(63) Continuation-in-part of application No. PCT/CN2019/074359, filed on Feb. 1, 2019.

(30) Foreign Application Priority Data

Feb. 9, 2018 (CN) .......................... 201810139361.2

(51) Int. Cl.
| | | |
|---|---|---|
| A61K 31/7004 | (2006.01) | |
| A61K 35/17 | (2015.01) | |
| A61P 35/00 | (2006.01) | |

(52) U.S. Cl.
CPC .......... *A61K 31/7004* (2013.01); *A61K 35/17* (2013.01); *A61P 35/00* (2018.01)

(58) Field of Classification Search
None
See application file for complete search history.

(56) References Cited

FOREIGN PATENT DOCUMENTS

| CN | 1202907 A | 12/1998 |
|---|---|---|
| CN | 103254212 A | 8/2013 |
| CN | 107501291 A | 12/2017 |
| CN | 108047282 A | 5/2018 |
| CN | 108785688 A | 11/2018 |
| CN | 107501291 B | 1/2020 |

OTHER PUBLICATIONS

Kaltgrad et al., Journal of the American Chemical Society—2008, vol. 130(14), pp. 4578-4579. (Year: 2008).*
International Search Report and Written Opinion with English Translation of ISR, cited in PCT/CN2019/074359 dated Apr. 24, 2019, 26 pages.
Prescher, H. et al., "Discovery of Multifold Modified Sialosides as Human CD22/Siglec-2 Ligands with Nanomolar Activity on B-Cells", ACS Chemical Bioiogy,vol. 9, No. (7), May 7, 2014 (May 7, 2014), 1-36, pp. 1444-1450.
Tal, G. et al., "The Effect of Haptens on Protein-Carrier Immunogenicity", Immunology,vol. 144, No. (1), Dec. 31, 2015 (Dec. 31, 2015), 1-36, pp. 116-126.
O'Reilly, M.K. et al., "Bifunctional CD22 Ligands Use Multimeric Immunoglobulins as Protein Scaffolds in Assembly of Immune Complexes on B Cells", Journal of the American Chemical Society,vol. 130, No. (24), Dec. 31, 2008 (Dec. 31, 2008), 1-36, pp. 7736-7745.
Nycholat, C. et al., "In Silico-Aided Design of a Glycan Ligand of Sialoadhesin for in Vivo Targeting of Macrophages", American Chemical Society, Sep. 11, 2012, 134, 15696-15699.
Zhang, et al., "Latest Research Progress of Tumor-targeting Contrast Agent in Magnetic Resonance Imaging", China Academic Journal Electronic Publishing House, 165-168, 2017 with English Abstract.
Rillahan, et al., "Disubstituted sialic acid ligands targeting siglecs CD33 and CD22 associated with myeloid leukaemias and B cell lymphomas†", Chem. Sci., 2014, 5, 2398-2406, www.rsc.org/chemicalscience.
Du, et al., "Metabolic glycoengineering: Sialic acid and beyond", Published by Oxford University Press, Glycobiology vol. 19 No. 12 pp. 1382-1401, 2009.
Peng, et al., "CD22 Ligands on a Natural N-Glycan Scaffold Efficiently Deliver Toxins to B-Lymphoma Cells", American Chemical Society, 2017, 12450-12458.
Zhang, et al., Clinical Glycobiology, Nov. 30, 2017, 5 pages.
Ren, et al., Biochemistry and Clinical Medicine, Dec. 31, 1993, 3 pages.

* cited by examiner

*Primary Examiner* — Traviss C McIntosh, III
(74) *Attorney, Agent, or Firm* — Cooper Legal Group, LLC (57) ABSTRACT

The present disclosure discloses carbohydrate derivatives used for surface modification of immune cells, use thereof, and method thereof. The carbohydrate derivatives are 9-carbon monosaccharide sialic acid derivatives modified at C9 position by targeting substituents. The surfaces of the immune cells (T cells, NK cells, macrophages, DC cells, B cells, or granulocytes) is modified by the carbohydrate derivatives to obtain modified immune cells, so that the modified immune cells can be used for treatment of tumors or other diseases to obtain good effects.

4 Claims, 12 Drawing Sheets

CARBOHYDRATE DERIVATIVES USED FOR SURFACE MODIFICATION OF IMMUNE CELLS, USE THEREOF AND METHOD THEREOF

RELATED APPLICATIONS

This application is a continuation in part of and claims priority to PCT Patent Application PCT/CN2019/074359, filed on Feb. 1, 2019, which claims priority to Chinese Patent Application 201810139361.2, filed on Feb. 9, 2018. PCT Patent Application PCT/CN2019/074359 and Chinese Patent Application 201810139361.2 are incorporated herein by reference.

FIELD OF THE INVENTION

The present disclosure relates to a technical field of chemical engineered cell therapeutics, and more particularly, the present disclosure relates to carbohydrate derivatives used for surface modification of immune cells and the use thereof.

BACKGROUND OF THE INVENTION

Cancer poses a serious threat to human health, and it is also an unsolved challenge in science. Once people get cancer, it is almost equivalent to a death sentence. Traditional treatments, such as surgery, radiotherapy, and chemotherapy, can inhibit the growth of cancer to a certain extent and prolong the survival time of patients, but traditional treatments cannot completely cure the cancer as a persistent disease. Since the $21^{st}$ century, as a newly crosscutting field, with the development of cancer immunology, cancer immunotherapy has emerged as a brand-new method of cancer treatment. Cancer immunotherapy has set off a green revolution in cancer treatment, which is expected to completely cure cancer as a persistent disease and has broad development prospect.

Cell therapy is one of the therapeutic methods with the most potential in cancer immunotherapy. It mainly includes lymphokine-activated killer cell therapy (LAK), tumor-infiltrating lymphocyte therapy (TIL), cytokine-induced killer cell therapy (CIK), dendritic antigen presenting cell therapy (DCCIK), tumor targeting antigen receptor T-cell therapy (TCR-T), and chimeric antigen receptor T-cell therapy (CAR-T). In current science technology, CAR-T cell therapy is the only method by which cancer cells can be completely eliminated, and it is also a hot spot of current research. CAR-T cells have a strong ability to kill tumor cells. However, due to its excessively strong immune killing effect, a large number of tumor cells are killed in a short time, which causes inflammation to be locally generated, a large number of cytokines to be released, resulting in a cytokine storm, and even causes organ failure in serious cases, thereby threatening a patient's life. Moreover, the existing CAR-T cell therapy requires complex operations of genetic engineering and takes a long time. It can only be used in an individual treatment, and cannot be widely used in commercial applications. The cost of existing CAR-T cell therapy is quite expensive.

SUMMARY OF THE INVENTION

To overcome the disadvantages of existing techniques, the present disclosure provides carbohydrate derivatives used for surface modification of immune cells.

The present disclosure further provides the use of the aforementioned carbohydrate derivatives.

The carbohydrate derivatives of the present disclosure are configured to be used in chemical engineered cell therapeutics. After the carbohydrate derivatives are co-cultured with immune cells, surfaces of the immune cells can be modified through metabolism of the immune cells to obtain surface-modified immune cells. The surface-modified immune cells can specifically target specific tumor cells or other pathological cells in vivo, then kill the specific tumor cells or the other pathological cells.

A first technical solution adopted by the present disclosure is as follows:

Carbohydrate derivatives used for surface modification of immune cells, wherein structures of the carbohydrate derivatives are as follows:

R is a benzene ring derivative targeted to CD22, a structure of R is at least one of:

In a preferred embodiment, the immune cells comprise at least one of T cells, NK cells, macrophages, DC cells, B cells, or granulocytes.

A second technical solution adopted by the present disclosure is as follows:

A use in a preparation of immune cells modified by carbohydrate derivatives, comprising absorbing the carbohydrate derivatives by the immune cells, metabolizing the carbohydrate derivatives to form CD22 ligand on a surface of a cell membrane of the immune cells, helping the immune cells to identify and target CD22-positive tumor cells, and killing the CD22-positive tumor cells.

Structures of the carbohydrate derivatives are as follows:

R is a benzene ring derivative targeted to CD22, a structure of R is at least one of:

In a preferred embodiment, the immune cells comprise at least one of T cells, NK cells, macrophages, DC cells, B cells, or granulocytes.

A third technical solution adopted by the present disclosure is as follows:

A method for modifying surfaces of immune cells by carbohydrate derivatives, comprising co-culturing the immune cells with the carbohydrate derivatives, metabolizing the carbohydrate derivatives by the immune cells, and modifying the surfaces of the immune cells by the carbohydrate derivatives.

Structures of the carbohydrate derivatives are as follows:

R is a benzene ring derivative targeted to CD22, a structure of R is at least one of:

In a preferred embodiment, the immune cells comprise at least one of T cells, NK cells, macrophages, DC cells, B cells, or granulocytes.

The technical solution provided by the present disclosure has the following advantages: the carbohydrate derivatives (sugar derivatives) of the present disclosure are sialic acid derivatives (one of 9-carbon monosaccharide) modified at C9 position by targeting substituents, and the surfaces of the immune cells (T cells, NK cells, macrophages, DC cells, B cells, or granulocytes) are modified by the carbohydrate derivatives to obtain a plurality of modified immune cells, so that the modified immune cells can be used for the treatment of tumors or other diseases to obtain good effects. Compared with the existing CAR-T cell therapy based on genetic engineering technology, the carbohydrate derivatives can be used to modify immune cells efficiently, can be used to produce similar products off-the-shelf on a large scale with low cost, and have significant commercial value.

DETAILED DESCRIPTION OF THE EMBODIMENTS

The present disclosure is further described with the combination of the accompanying drawings together with the embodiments.

A method for using the sugar derivatives of the present disclosure in Chemical Engineered Cell Therapeutics (CECT), comprising:

1) Acquisition and Culture of Immune Cells

Obtaining immune cells, the immune cells mainly comprises at least one of T cells, NK cells, macrophages, DC cells, B cells, or granulocytes. Taking a plurality of the most lethal CD8 T cells as an example, the plurality of CD8 T cells were isolated from peripheral blood of a donor by flow cytometry and cultured in a first cell growth medium to produce a plurality of effector cells in a sufficient amount.

2) Co-Culturing the Immune Cells and Targeting Molecules with Targeting Groups Adding the targeting molecules with the targeting groups into a second cell growth medium, co-culturing the targeting molecules and the immune cells for a certain period, metabolizing the plurality of effector cells, labelling surfaces of the plurality of effector cells with the targeting molecules to obtain a plurality of targeting cells, and evaluating and optimizing an efficiency of labelling surfaces of the plurality of effector cells.

3) Returning the Plurality of Targeting Cells

Injecting the plurality of targeting cells intravenously and directly into the blood in a certain amount and frequency to treat a corresponding tumor.

The chemical structural formulas of the targeting molecules are as follows:

R is a benzene ring derivative targeted to CD22, a structure of R is at least one of:

An intracellular metabolic mechanism of the targeting molecules is as follows:

The targeting molecules can be eventually presented to a surface of the targeting cells through intracellular metabolic pathway of sialic acid. Taking the sialic acid (N-acetylneuraminic acid) metabolic pathway as an example, absorbing these small molecules by the cells, entering into the cells, then transforming into CMP-Neu5Ac in nuclei of the cells by CMP-Neu5Ac synthases, then transferring into Golgi bodies, in which sialic acids are transferred from CMP-Neu5Ac onto newly synthesized glycoconjugates, being added to an end of glycoproteins or glycolipids, and being presented on the surface of the cell membrane. If a hydroxyl group at the C-9 position of sialic acid is replaced by other substituent groups, expressing these small molecules at the end of glycoprotein of the cell membrane in the form of sialic acid derivatives through intracellular metabolic transformation to obtain cells modified with specific substituent groups, thus completing the modification of the surface of the cells.

Embodiment 1: A Method for Synthesizing BPC-sia

A method for synthesizing BPC-sia is as follows:

1. Adding sialic acid (formula 1, a first compound) (15 g) in anhydrous methanol (200 mL) to obtain a sialic acid solution, mixing the sialic acid solution with trifluoroacetic acid (7 mL) to obtain a first mixture solution, stirring the first mixture solution at room temperature for about 7 days until the first mixture solution turns clear, and concentrating the first mixture solution in vacuum to obtain sialic acid methyl ester (a first residue, 14 g). The sialic acid methyl ester is an off-white solid. Then dissolving the sialic acid methyl ester in anhydrous pyridine (100 mL) to obtain a mixture, adding paratoluensulfonyl chloride (10 g) into the mixture in an ice bath to obtain a second mixture solution, stirring the second mixture solution at room temperature overnight, concentrating the second mixture solution in vacuum to obtain a second residue, and purifying the second residue by a silica gel column to obtain a second compound (formula 2) (18 g). The second compound is an off-white solid.

2. Adding the second compound (14 g) in anhydrous methane (150 mL) to obtain a solution of the second compound, adding sodium azide (8 g) to the solution of the second compound to obtain a third mixture solution, refluxing the third mixture solution overnight, concentrating the third mixture solution in vacuum to obtain a third residue, and purifying the third residue by a silica gel column to obtain a third compound (formula 3). The third compound is a light yellow solid.

3. Dissolving the third compound in anhydrous MeOH (20 mL), hydrogenating the third compound with Pd/C (10 wt % palladium on activated carbon) and hydrogen ($H_2$), then adding acetyl chloride (0.6 mL) to obtain a fourth mixture solution, stirring the fourth mixture solution overnight at room temperature, filtrating the fourth mixture solution with diatomite, collecting filtrate, concentrating the filtrate in vacuum to obtain a fourth residue, dissolving the fourth residue in dimethyl formamide (10 mL), then adding EDC.HCl (1-Ethyl-3-(3-dimethylaminopropyl) carbodiimide hydrochloride, 2 g), HOBT (Hydroxybenzotriazole, 1.4 g), TEA (Triethylamine, 3.6 mL), and compound R (formula BPC, 2.1 g) to obtain a fifth mixture solution, stirring the fifth mixture solution for 12 hours at room temperature, concentrating the fifth mixture solution in vacuum to obtain a fifth residue, and purifying the fifth residue by a silica gel column to obtain a fourth compound (formula 4, 2.6 g). The fourth compound is a light yellow solid.

4. Dissolving the fourth compound (548 mg) in methanon (5 mL) to obtain a solution of the fourth compound, adding NaOH (5 mL, 2 M) into the solution of the fourth compound to obtain a sixth mixture solution, stirring the sixth mixture solution for 20 minutes, adjusting the pH of the sixth mixture solution to 5-6 with 2 M HCl, concentrating the sixth mixture solution in vacuum to obtain a sixth residue, and purifying the sixth residue by a silica gel column to obtain a fifth compound (BPC-sia, formula 5, 294 mg).

Embodiment 2

A method for synthesizing MPB-sia is as follows:

MPB-sia
(8)

1. Dissolving a sixth compound (formula 6, 3 g) in dimethyl formamide (10 mL) to obtain a solution of the sixth compound, adding EDC.HCl (1-Ethyl-3-(3-dimethylaminopropyl) carbodiimide hydrochloride, 2 g), HOBT (Hydroxybenzotriazole, 1.4 g), TEA (Triethylamine, 3.6 mL), and compound MPB (formula MPB, 2.1 g) to obtain a seventh mixture solution, stirring the seventh mixture solution for 12 hours at room temperature, concentrating the seventh mixture solution in vacuum to obtain a seventh residue, and purifying the seventh residue by a silica gel column to obtain a seventh compound (formula 7, 1.6 g). The seventh compound is a light yellow solid.

2. Dissolving the seventh compound (1.6 g) in THF (Tetrahydrofuran, 15 mL) to obtain a solution of the seventh compound, adding NaOH (500 mg, in 8 mL water) into the solution of the seventh compound to obtain an eighth mixture solution, stirring the eighth mixture solution for 20 minutes, adjusting the pH of the eighth mixture solution to 5-6 with 2 M HCl, concentrating the eighth mixture solution in vacuum to obtain an eighth residue, and purifying the eighth residue by HPLC (High Performance Liquid Chromatography) to obtain an eighth compound (formula 8, 600 mg). The eighth compound is a light yellow solid.

Embodiment 3: Modifying NK-92 Cells by BPC-sia for Treatment of B Lymphoma

1. Modifying NK-92 Cells by BPC-sia (Also Known as BPCA-sia)

Culturing ATCC (American Type Culture Collection)-derived NK-92 (ATCC® CRL2407™) cells (also known as NK-92 cell lines) in a first alpha-MEM growth medium (comprising 12.5% (v/v) newborn bovine serum, 12.5% (v/v) horse serum, 100 U/ml recombinant IL-2) in an incubator with 5% (v/v) $CO_2$ atmosphere at 37° C., then replacing the first alpha-MEM growth medium with a second alpha-MEM growth medium (comprising 100 μM BPC-sia), continuing to culture for 72 hours, and washing for three times to obtain BPC-sia modified NK-92 cells (NK-92 BPCA).

2. Localization of BPC-sia on Surfaces of NK-92 Cells

Figure 1:
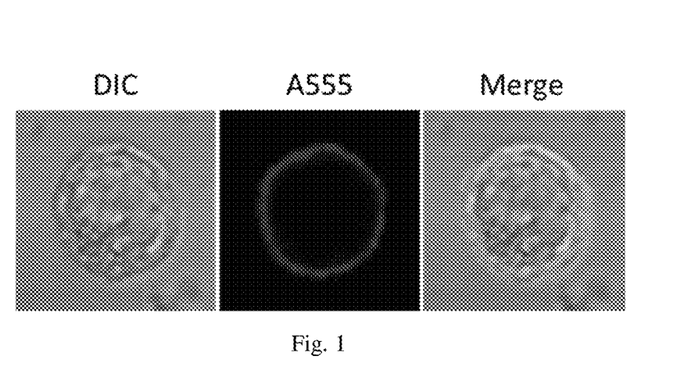
FIG. 1 illustrates NK-92 cells modified by BPC-sia in embodiment 3 of the present disclosure.

Culturing the BPC-sia modified NK-92 cells in a third alpha-MEM growth medium with 0.2 mg/mL rhCD22-His protein (11958H08H5) on ice for half an hour, and adding 6×-His Tag Antibody-dye (MA1-135-A555) to fluorescently label the BPC-sia modified NK-92 cells. A volume ratio of 6×-His Tag Antibody-dye to rhCD22-His protein is 1:50. After culturing on ice for half an hour, performing confocal observation (exciting at 555 nm, emitting at 565 nm). Results of the confocal observation are shown in FIG. 1. Fluorescent signals of antibodies could be detected on the surfaces the BPC-sia modified NK-92 cells, which indicates that BPC-sia can be expressed on the surfaces of cell membranes through metabolic pathway of sialic acid.

Because BPC-sia can effectively target CD22, BPC-sia modified NK-92 cells can be obtained by co-incubating NK-92 cells with BPC-sia, which is very important for targeting CD22-positive cells to play a killing function.

3. Cytotoxicity Test In Vitro

Figure 2:
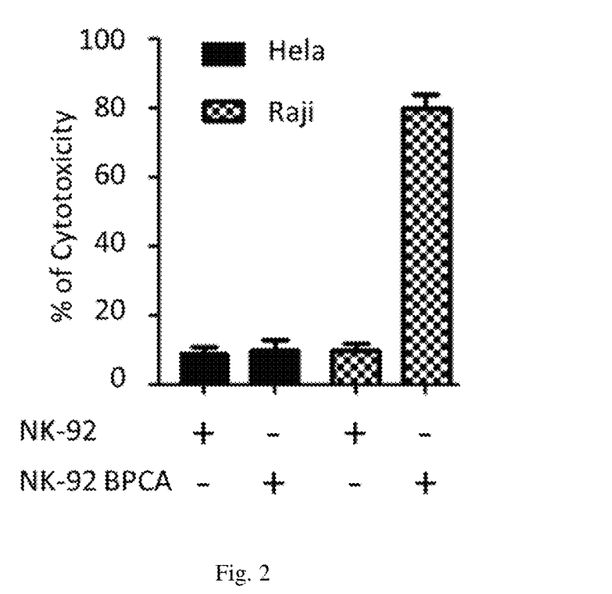
FIG. 2 illustrates an in vitro cytotoxicity experiment in embodiment 3 of the present disclosure.

Respectively mixing Hela cells or Raji Burkitt lymphocytes with BPC-sia modified NK-92 cells (test group) or original NK-92 cells (control group) at a quantity ratio of 1:10, after co-culturing in an incubator at 37° C. for 5 hours, detecting a content of lactate dehydrogenase in supernatant by a detection kit of lactate dehydrogenase, and calculating the cytotoxicity with reference to the control group. Results of the cytotoxicity are shown in FIG. 2. Lactate dehydrogenase (also known as LDH) is an enzyme existing in cytoplasm. When cell membranes are damaged, LDH will be released into a growth medium. When NK cells are coupled to target cells, perforin and NK cytotoxic factors will be released, which will destroy membranes of the target cells and cause the release of LDH. Therefore, a detected content of LDH in the growth medium can be used to show killing toxicity of NK cells or BPC-sia modified NK-92 cells. As can be seen from FIG. 2, since there is no CD22 receptor on surfaces of Hela cells, the NK-92 cells and the BPC-sia modified NK-92 cells have no obvious killing activity against Hela cells. Raji Burkitt lymphocytes are Burkitt lymphoma cells with positive expression of CD22 on their surface. BPC-sia modified NK-92 cells have increased killing toxicity relative to Raji Burkitt lymphocytes.

4. Therapeutic Effect on Leukemia Mouse Model

Injecting $1\times10^6$ Raji cells into a tail vein of each NSG (6-8 weeks old) mouse to establish a leukemia mouse model. From the third day, injecting $5\times10^6$ NK-92 cells (taken as NK-92 cells group) or BPC-sia modified NK-92 cells (taken as BPC-sia modified NK-92 cells group) into the tail vein every two days. Injecting PBS (Phosphate-buffered saline) into a tail vein of each NSG (6-8 weeks old) mouse of the control group. Each group comprises 15 mice. The survival rate of each group is observed, and the results of the survival rate are shown in FIG. 3.

Figure 3:
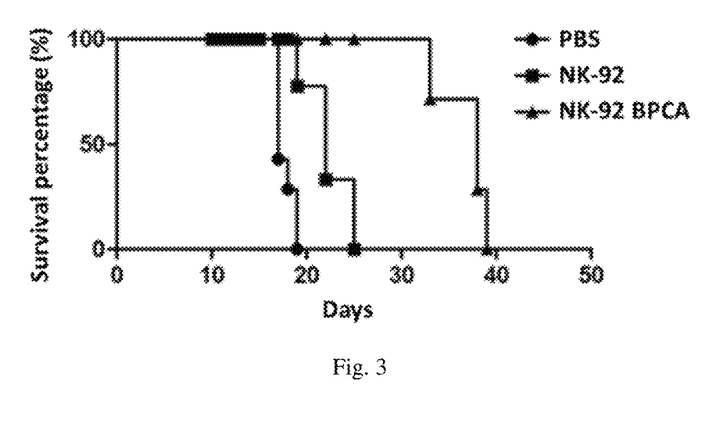
FIG. 3 illustrates a survival curve of NSG mice in embodiment 3 of the present disclosure.

As can be seen from FIG. 3, after establishing the leukemia mouse model, a longest survival period of NSG mice is about 19 days. When injecting NK-92 cells into the tail vein, a survival rate of NSG mice can be slightly prolonged. When injecting BPC-sia modified NK-92 cells into the tail vein, a longest survival period of NSG mice can be prolonged to about 40 days. The aforementioned results indicate that BPC-sia modified NK-92 cells have good targeting and tracking killing activity on leukemia cells in vivo, which can be used for reference in further clinical trials.

Embodiment 4: Treating B Lymphoma by BPC-sia Modified CD8 T Cells

1. Modifying CD8 T Cells by BPC-sia (also known as BPCA-sia) Separating from peripheral blood of healthy donors to obtain CD8 T cells by flow cytometry. Culturing CD8 T cells on a first RPMI-1640 growth medium (comprising 10% (v/v) FBS and 100 IU/ml recombinant IL-2) at 37° C. in an incubator with 5% (v/v) $CO_2$ atmosphere, then replacing the first RPMI-1640 growth medium with a second RPMI-1640 growth medium (comprising 100 mu BPC-sia), continuously culturing for 72 hours, and washing for three times to obtain BPC-sia modified CD8 T cells.

2. Localization of BPC-sia on Surfaces of CD8 T Cells

Figure 4:
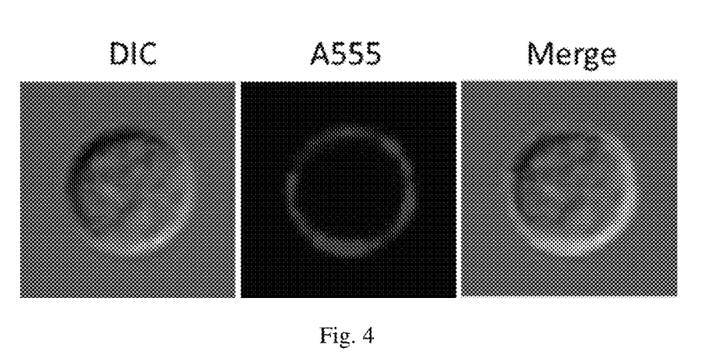
FIG. 4 illustrates CD8 T cells modified by BPC-Neu5Ac in embodiment 4 of the present disclosure.

Culturing the BPC-sia modified CD8 T cells in a third RPMI-1640 growth medium comprising rhCD22-His protein (11958H08H5) with a concentration of 0.2 mg/mL for 2 hours at 37° C., washing three times, and adding 6×-His Tag Antibody-dye (MA1-135-A555) to fluorescently label the BPC-sia modified CD8 T cells. A volume ratio of 6×-His Tag Antibody-dye to rhCD22-His protein is 1:50. After culturing for 1 hour at 37° C., performing confocal observation (exciting at 555 nm, emitting at 565 nm). Because BPC-sia can effectively target CD22, and BPC-sia can be expressed on the surfaces of cell membranes through intracellular metabolic pathway of sialic acid, BPC-sia can be effectively combined with rhCD22-His protein, and positions of BPC-sia can be displayed after labeling by fluorescence probes. It can be seen from FIG. 4, after co-culturing BPC-sia with CD8 T cells, BPC-sia can be effectively expressed to surfaces of CD8 T cells, which is very important for targeting CD22 positive cells to play a killing function.

3. Cytotoxicity Test In Vitro

Figure 5:
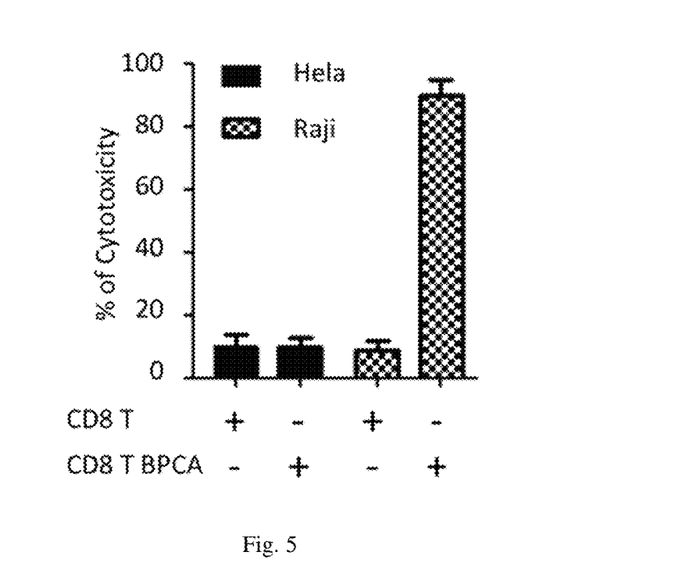
FIG. 5 illustrates an in vitro cytotoxicity experiment in embodiment 4 of the present disclosure.

Respectively mixing Hela cells or Raji Burkitt lymphocytes with BPC-sia modified CD8 T cells (test group) or original CD8 T cells (control group) in a quantity ratio of 1:10. After co-culturing in an incubator at 37° C. for 24 hours, detecting a content of lactate dehydrogenase in supernatant by a detection kit of lactate dehydrogenase, and calculating the cytotoxicity with reference to the control group. Results of the cytotoxicity are shown in FIG. 5.

Lactate dehydrogenase (also known as LDH) is an enzyme existing in cytoplasm. When cell membranes are damaged, LDH will be released into growth medium. When CD8 T cells are coupled to target cells, perforin and granulase will be released, which will destroy membranes of the targeting cells and cause the release of LDH. Therefore, a detected content of LDH in the growth medium can be used to show killing toxicity of CD8 T cells or BPC-sia modified CD8 T cells. As can be seen from FIG. 5, since there is no CD22 receptor on surfaces of Hela cells, the original CD8 T cells and the BPC-sia modified CD8 T cells have no obvious killing activity. Raji Burkitt lymphocytes are Burkitt lymphoma cells, and an expression of CD22 is positive on surfaces of Raji Burkitt lymphocytes. A cytotoxicity of BPC-sia modified CD8 T cells relative to Raji Burkitt lymphocytes is significantly increased.

4. Therapeutic Effect on Leukemia Mouse Model

Injecting $1\times10^6$ Raji cells into a tail vein of each NSG (6-8 weeks old) mouse to establish a leukemia mouse model. From the third day, injecting $5\times10^6$ CD8 T cells (taken as CD8 T cells group) or BPC-sia modified CD8 T cells (taken as BPC-sia modified CD8 T cells group) into the tail vein every two days. Injecting PBS into a tail vein of NSG (6-8 weeks old) mice of the control group. Each group comprises 15 mice. The survival rate of each group is observed, and the results of the survival rate are shown in FIG. 6.

Figure 6:
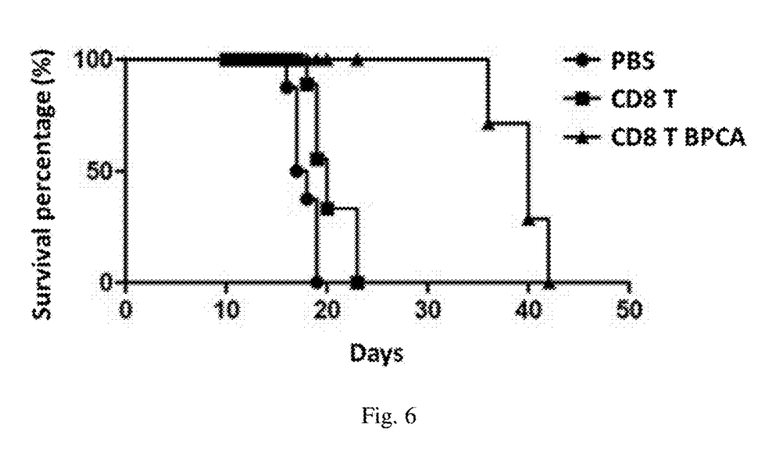
FIG. 6 illustrates a survival curve of NSG mice in embodiment 4 of the present disclosure.

As can be seen from FIG. 6, after establishing the leukemia mouse model, a longest survival time of leukemia mice is about 19 days. When injecting CD8 T cells into the tail vein, a survival rate of NSG mice can be slightly prolonged. When injecting BPC-sia modified CD8 T cells into the tail vein, a longest survival time of NSG mice can be prolonged to about 42 days. The aforementioned results indicate that BPC-sia modified CD8 T cells have a good targeting and tracking killing activity on leukemia cells in vivo.

Embodiment 5: Modifying NK-92 Cells by MPB-sia for Treatment of B Lymphoma

1. Modifying NK-92 Cells by MPB-sia

Culturing ATCC (American Type Culture Collection)-derived NK-92 (ATCC® CRL2407™) cells (also known as NK-92 cell lines) on a fourth alpha-MEM growth medium (comprising 12.5% (v/v) newborn bovine serum, 12.5% (v/v) horse serum, 100 U/ml recombinant IL-2) in an incubator with 5% (v/v) $CO_2$ atmosphere at 37° C., then replacing the fourth alpha-MEM growth medium with a fifth alpha-MEM growth medium (comprising 2 mMPB-sia), continuing to culture for 48 hours, and washing for three times to obtain MPB-sia modified NK-92 cells, which is referred to as MsNK-92 cells.

2. Analyzing CD22 Ligand on Surfaces of NK-92 Cells

Figure 7:
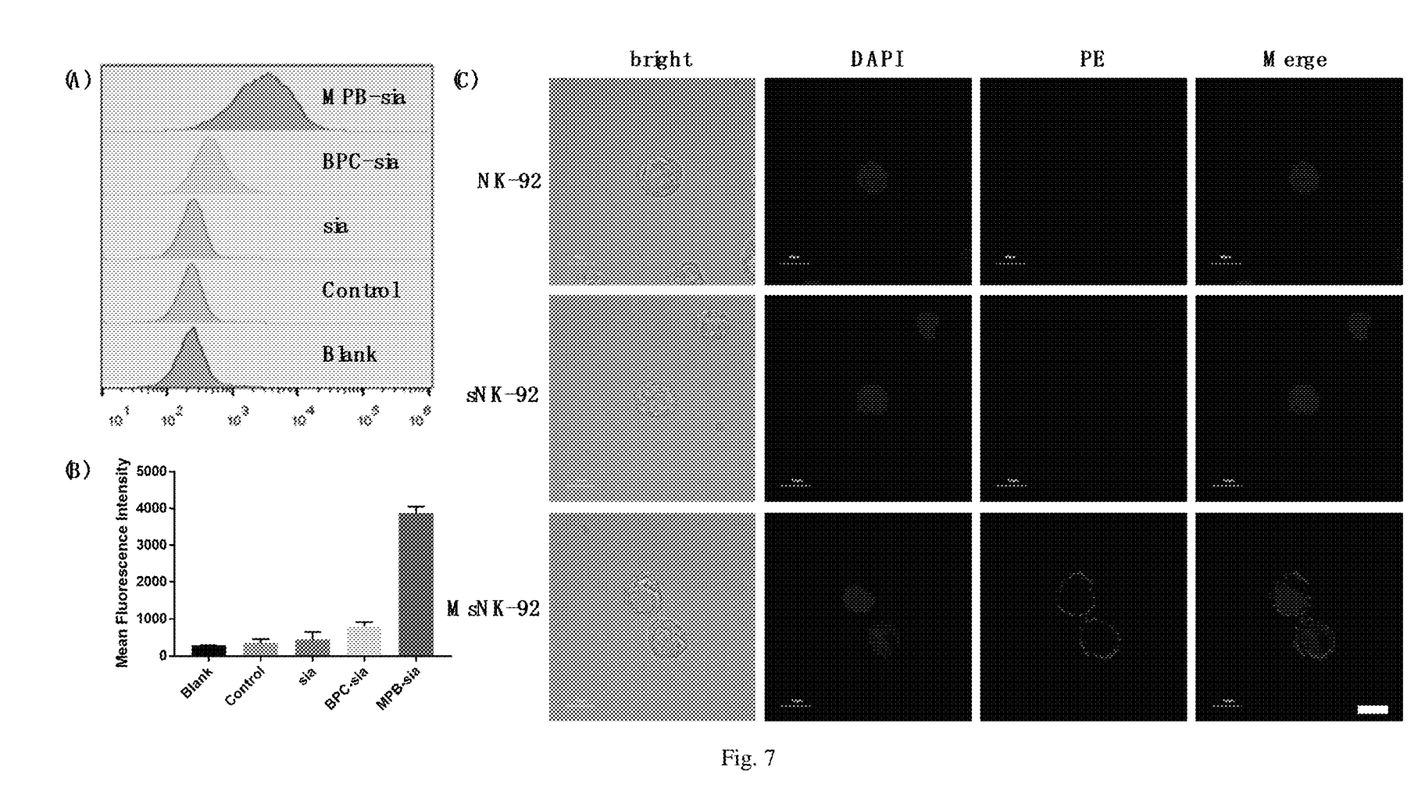
FIG. 7 illustrates MPB-sia or BPC-sia metabolic engineered onto cell surfaces of NK-92 cells in embodiment 5 of the present disclosure.

Washing MPB-sia or BPC-sia modified NK-92 cells with PBS buffer for three times, adding 100 µL, PBS, adding 1 µg CD22-fc to obtain a first mixture, then culturing the first mixture on ice for 30 minutes, washing three times with PBS buffer, then adding anti-CD22-PE to obtain a second mixture, culturing the second mixture on ice for 30 minutes, washing three times, then collecting cells, quantifying the extent of CD22 binding by flow cytometry analysis, and imaging by confocal microscopy. As shown in FIG. 7, native NK-92 cells had little binding with CD22 over the background, similar to free sialic acid (sia) treated NK-92 cells. In comparison with BPC-sia enhanced CD22 binding to NK-92 cells, MPB-sia incubation led to the greatest improvement in cellular binding by CD22 (FIGS. 7A and 7B). In FIG. 7C, native NK-92 cells or NK-92 cells treated with free sialic acid (sNK-92) did not present much Phycoerythrin (PE) fluorescence upon incubation with CD22 and PE labeled anti-CD22 mAb (FIG. 7C). In contrast, apparent PE fluorescence was observed on the surface of MPB-sia treated cells (MsNK-92), with fluorescence intensities distributed over the whole cell surface (FIG. 7C). These results suggest that NK-92 cells could be metabolically glycoengineered with sialic acid derivatives such as MPB-sia or BPC-sia to install CD22 ligands on cell surfaces.

Figure 8:
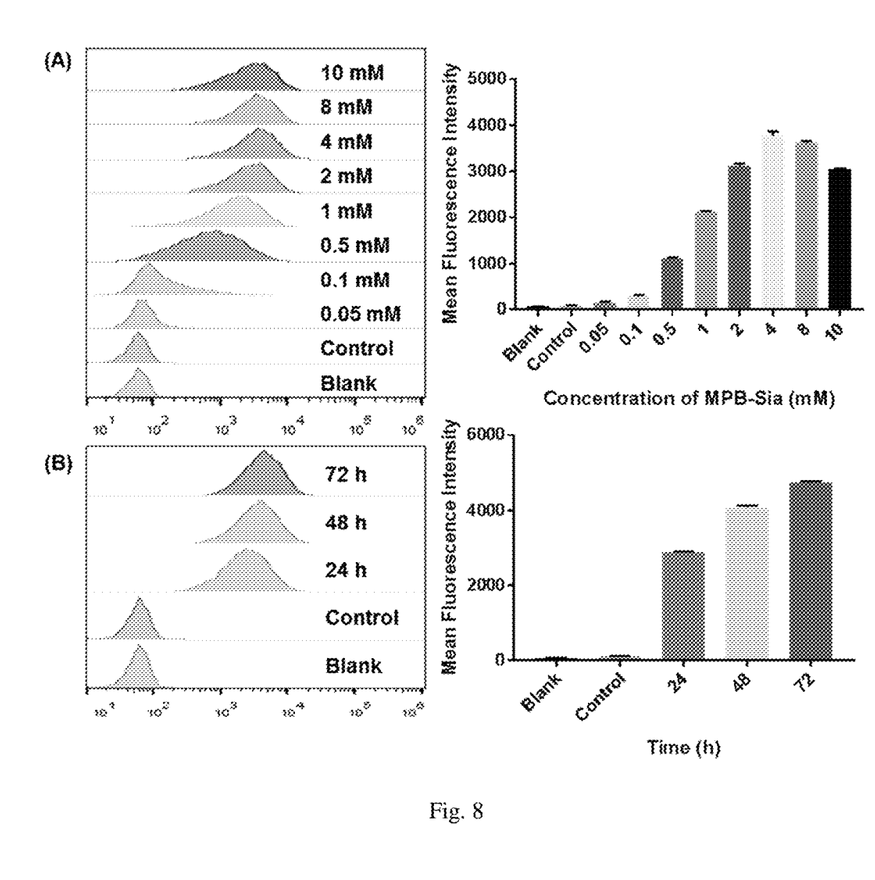
FIG. 8 illustrates metabolic incorporation of MPB-sia onto the cell surfaces NK-92 cells in embodiment 5 of the present disclosure.
Figure 9:
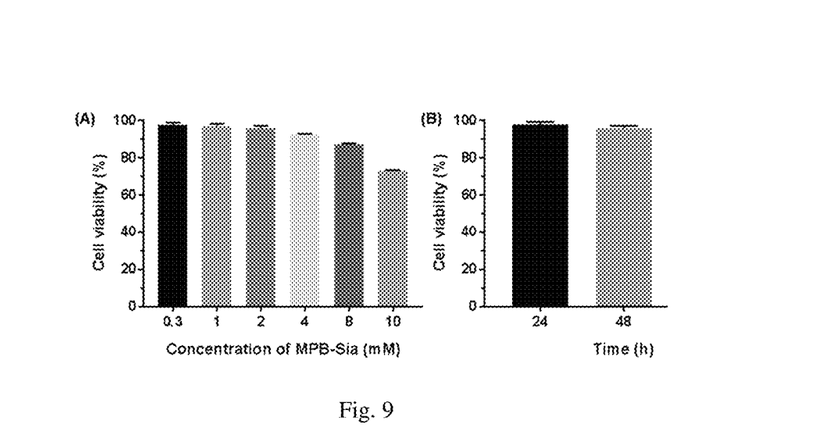
FIG. 9 illustrates viability effects of MPB-sia on NK-92 cells in embodiment 5 of the present disclosure.
Figure 10:
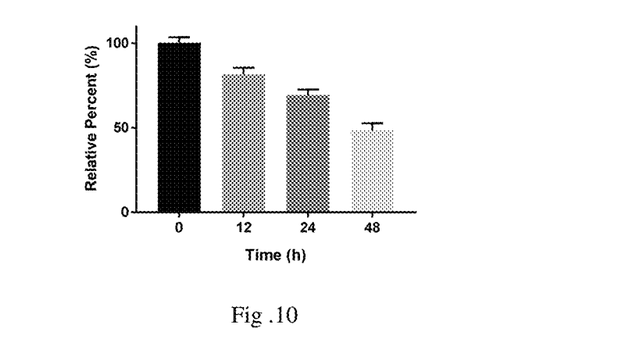
FIG. 10 illustrates persistence of CD22 ligands after metabolic engineering in embodiment 5 of the present disclosure.
Figure 11:
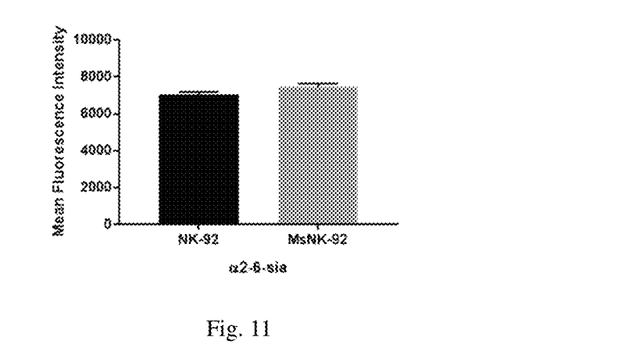
FIG. 11 illustrates levels of α2-6-sia linkage on the cell surfaces of NK-92 cells before and after metabolic engineering in embodiment 5 of the present disclosure.

CD22 ligands were metabolically engineered onto NK-92 cells by MPB-sia in a dose-dependent and time-dependent manner (FIG. 8). Increasing the concentration of MPB-sia enhanced the levels of CD22 ligand expression on cell surfaces reaching a maximum at 4 mM of MPB-sia at 24 hours (FIG. 8A). Increasing the incubation time to 48 and 72 hours led to higher levels of CD22 binding to NK-92 cells (FIG. 8B). Cell viability studies showed slight decreases of cell viability when concentrations of MPB-sia were over 4 mM (FIG. 9A). NK-92 cells ($5 \times 10^5$ per sample) were incubated with 2 mM of MPB-sia for 48 hours; cells also keep a high cell viability (FIG. 9B). Next, the persistence of CD22 ligands on engineered NK-92 cells was analyzed. Upon removal of MPB-sia from the cell culture medium, 50% of CD22 binding remained on NK-92 cells after 48 hours (FIG. 10). As CD22 prefers α2-6-sia linkages, the levels of α2-6-siaglycans on engineered NK-92 cells were determined by staining with Fluorescein isothiocyanate labeled (FITC-labeled) α2-6-sia binding plant lectin *Sambucus nigralectin* (SNA) (FIG. 11). There were no significant changes of SNA staining before or after glyco-engineering, suggesting little influence on the overall amounts of α2-6-sialinkages by MPB-sia incubation.

3. Cytotoxicity Test In Vitro

Figure 12:
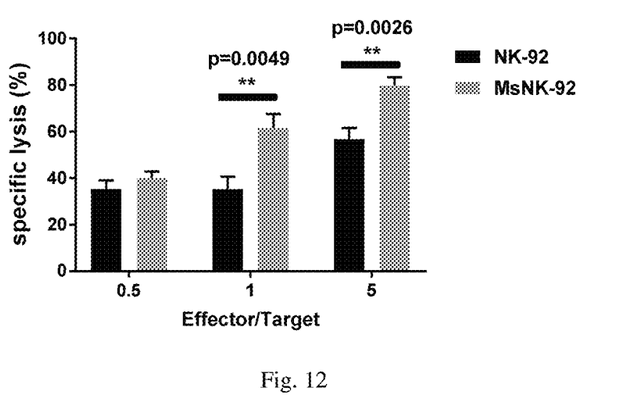
FIG. 12 illustrates effects of NK-92 cells and MsNK-92 cells on killing raji-luc cells under different effector-cell to target-cell ratios (Effector/Target) in embodiment 5 of the present disclosure.
Figure 13:
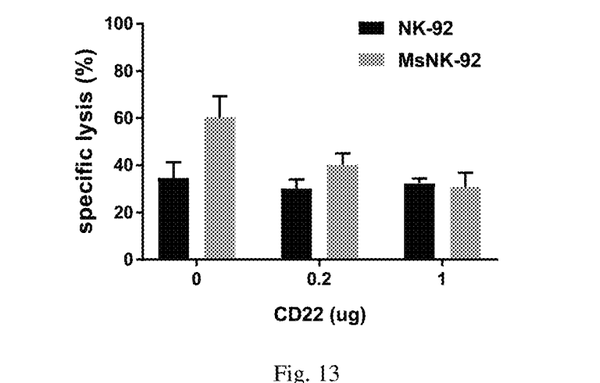
FIG. 13 illustrates effects of NK-92 cells and MsNK-92 cells on killing Raji cells having different CD22 concentrations in embodiment 5 of the present disclosure.

First, constructing human B lymphoma cells (raji-luc) stably expressing firefly luciferase. CD22 expressing on surfaces of human B lymphoma cells is positive. Then mixing human B lymphoma cells with NK-92 cells or MsNK-92 cells in different quantity ratios to obtain different groups. For each of the groups, respectively culturing at 37° C. for 5 hours, detecting a luciferase content in the remaining cells by a detection kit of firefly luciferase, and quantifying a cytotoxicity of NK-92 cells or MsNK-92 cells. Results of the cytotoxicity are shown in FIG. 12. Killing activity of MPB-sia modified NK-92 (MsNK-92) significantly increased on raji-luc when a ratio the Effector cells/Targeting cells is 1 or 5. This is because surfaces of MsNK-92 cells have a stronger ability to recognize and couple to CD22, which can help MsNK-92 cells to fully unleash their natural killing ability. When a quality of MsNK-92 cells increases, the killing activity is gradually enhanced. In order to further verify that the enhancement of killing ability is due to modification of MPB-sia, NK-92 cells or MsNK-92 cells are blocked by CD22. For example, the NK-92 cells or MsNK-92 cells co-cultured with CD22 for 30 minutes and then co-cultured with raji-luc. The results of cytotoxicity are shown in FIG. 13. An addition of CD22 had no effect on killing raji-luc activity of NK-92 cells, but had a concentration-dependent effect on killing raji-luc activity of MPB-sia modified NK-92 (MsNK-92). When an additive amount of CD22 increases, the killing activity of MsNK-92 on raji-luc decreases gradually. When CD22 concentration is 1 µg, the killing activity of MsNK-92 on raji-luc is equal to that of conventional unmodified NK-92. Therefore, the aforementioned experiments show that, when modifying by MPB-sia, the killing activity of NK-92 on cells expressing CD22 increases.

Figure 14:
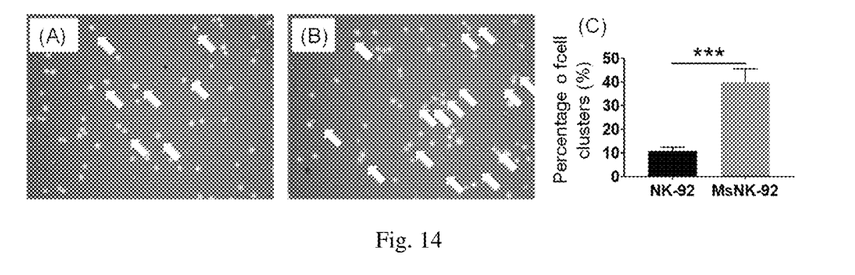
FIG. 14 illustrates Glyco-engineered NK-92 cells binding with CD22+ in embodiment 5 of the present disclosure.
Figure 15:
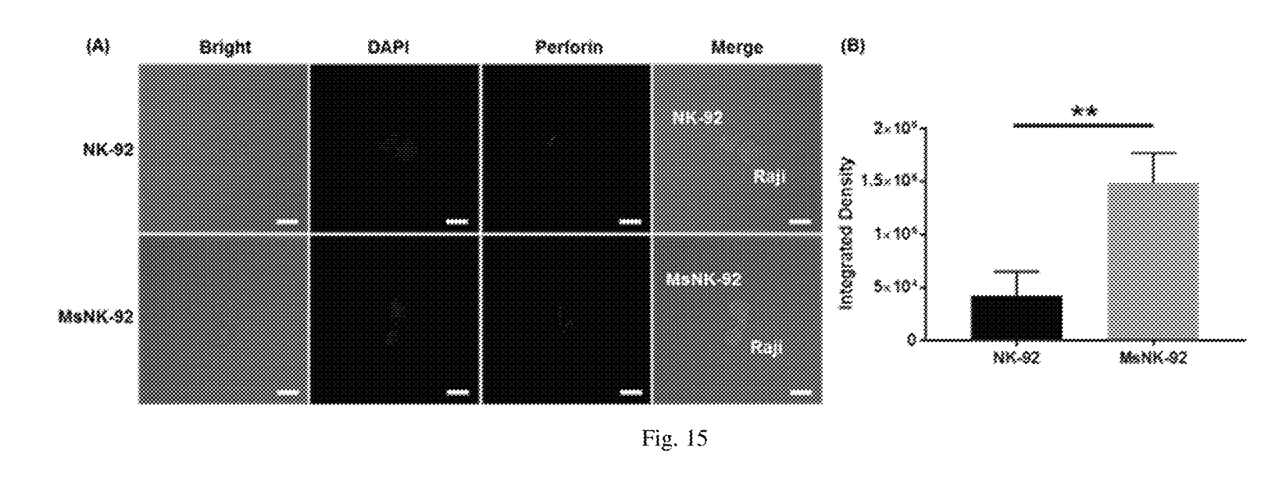
FIG. 15 illustrates complex formation between NK-92 cells and Raji cells investigated by confocal microscopy in embodiment 5 of the present disclosure.
Figure 16:
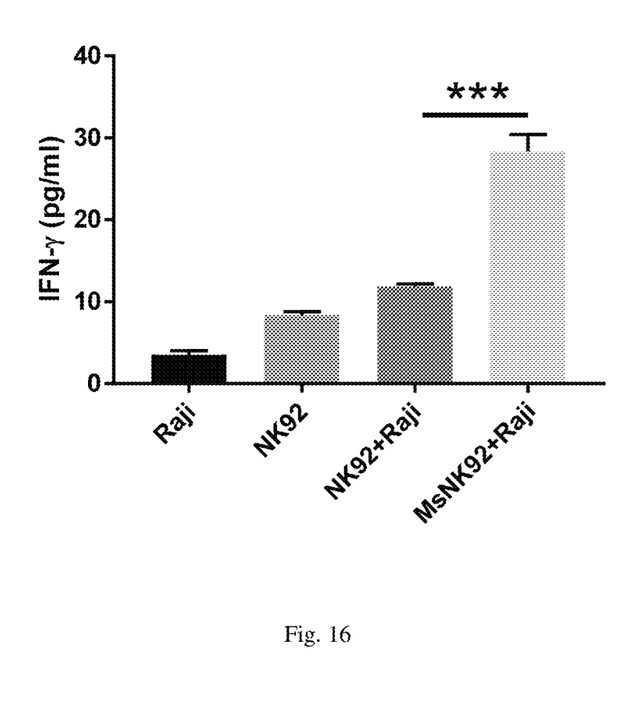
FIG. 16 illustrates IFN-γ production by Glyco-engineered NK-92 cells when stimulated with CD22+Raji cells in embodiment 5 of the present disclosure.

4. The Enhanced Killing Mechanism of Glyco-Engineered NK-92 Cells Against Raji Cells To gain a deeper understanding of the mode of action against Raji, glyco-engineered NK-92 cells were incubated with Calcein-AM labeled Raji cells, and imaged by fluorescence microscopy (FIG. 14). If NK-92 cells can bind with Raji, cell clusters would be formed around unlabeled NK-92 cells. Significantly higher percentages of glyco-engineered NK-92 cells were found clustered with Raji cells compared with native NK-92 cells and Raji cells, which could be attributed to the CD22 ligands on the glyco-engineered NK-92 increasing the binding affinity with Raji. Upon binding with target cells, NK cells can release cytotoxic granules containing perforin or pro-inflammatory cytokines, such as IFN-γ, to kill the target cells. Confocal imaging of the NK-92 and Raji cells complexes showed an increased number of cytotoxic granules at the immunological synapse in metabolic glycoengineered NK-92 cells when bound with Raji cells (FIG. 15), which indicated glycoengineered NK-92 cells were activated after initial binding. To further confirm the activation of glycoengineered NK-92, the IFN-γ release was detected. The glycoengineered NK-92 generated higher levels of pro-inflammatory cytokine IFN-γ compared with the unengineered parental NK-92 (FIG. 16).

5. Therapeutic Effect on Lymphoma Mouse Model

Figure 17:
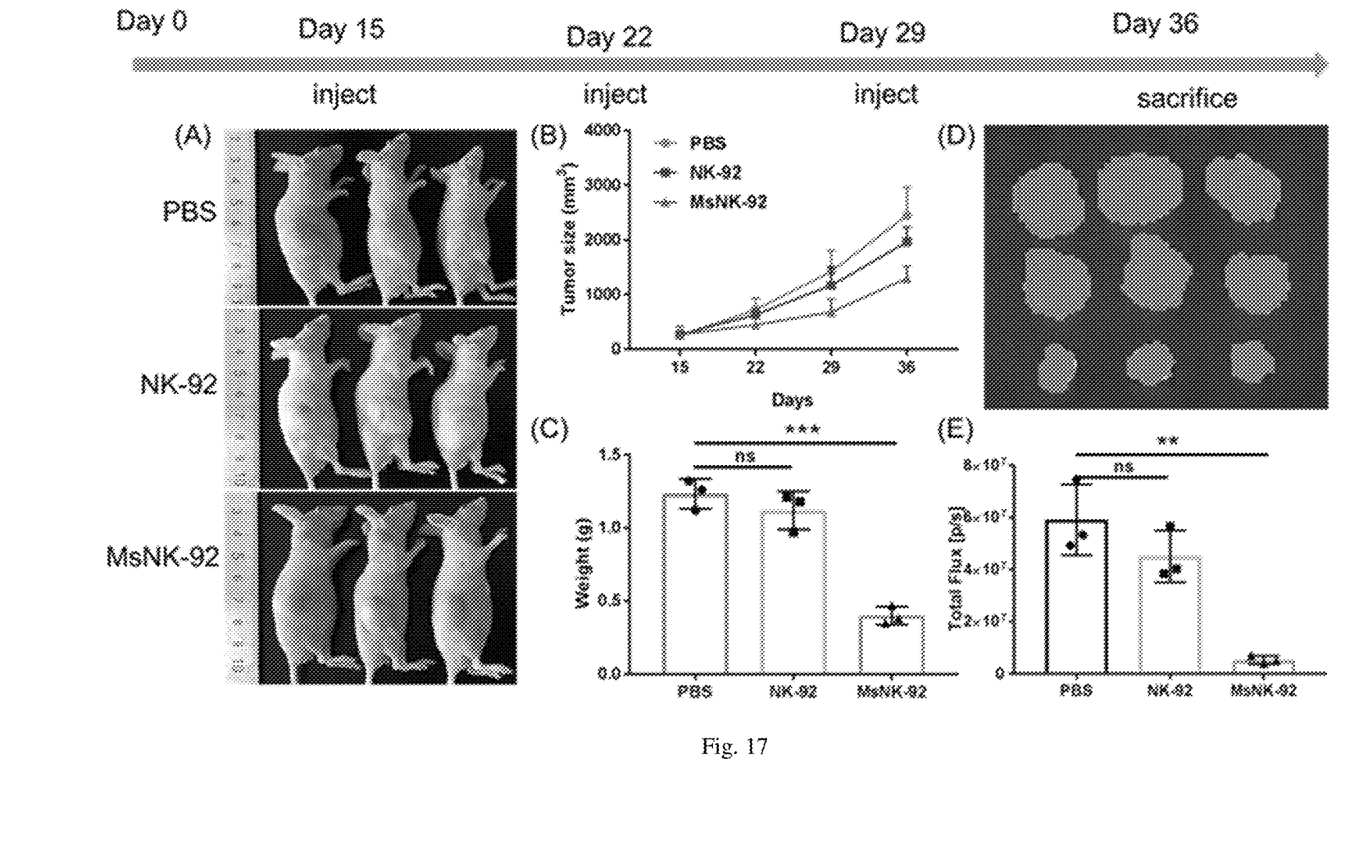
FIG. 17 illustrates a therapeutic data diagram of nude mice with subcutaneous solid tumors in embodiment 5 of the present disclosure.

As a test group, subcutaneously injecting $5 \times 10^6$ Raji-luc cells into each nude mouse aged 6-8 weeks, then injecting MsNK-92 cells in situ on the $15^{th}$, $22^{nd}$ and $29^{th}$ day, and measuring a size of each of the tumors. As a control group, subcutaneously injecting PBS in a same volume and a same quality of Raji-luc cells as the test group, and then injecting NK-92 cells without modification. On the $36^{th}$ day, dissecting the mice of the test group and the control group, measuring a volume and a weight of each of the tumors, and detecting a fluorescence intensity of each of the tumors. As shown in FIG. 17, a growth rate of each of the tumors in mice injected with MsNK-92 was significantly slower than that in control group (FIG. 17B). The volume and weight of the tumors were also significantly smaller than those of the control mice (FIG. 17A, C, D, E). Therefore, the experimental results showed that MPB-sia modified NK cells could significantly enhance anti-solid tumor activity.

6. Therapeutic Effect on Leukemia Mouse Model

Injecting 1×10⁶ Raji cells into a tail vein of NOD-SCID (6-8 weeks old) mice to establish leukemia model. From the second day, injecting 1×10⁷ NK-92 cells (taken as NK-92 cells group) or MPB-sia modified NK-92 cells (taken as BPC-sia modified NK-92 cells group) into the tail vein every two days. Injecting PBS into a tail vein of NOD-SCID (6-8 weeks old) mice of the control group. Each group comprises 10 mice. The survival rate of each group is observed, and the results of the survival rate are shown in FIG. 18.

Figure 18:
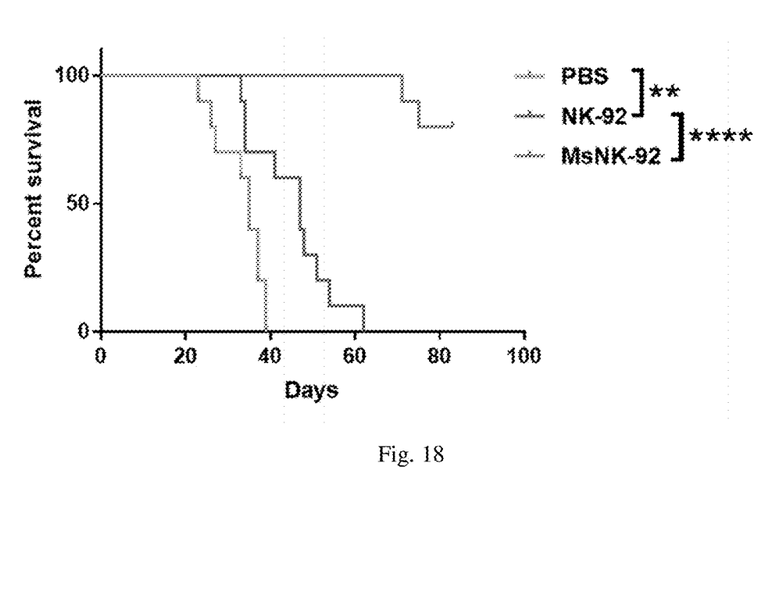
FIG. 18 illustrates a survival curve of NOD-SCID mice in embodiment 5 of the present disclosure.

As can be seen from FIG. 18, after establishing the leukemia mouse model, a longest survival period of the mice is about 40 days. When injecting NK-92 cells into the tail vein, a survival period of NSG mice can be slightly prolonged. When injecting MPB-sia modified NK-92 cells into the tail vein, a longest survival period of NSG mice can be prolonged to about 80 days. The aforementioned results indicate that MPB-sia modified NK-92 cells have a good targeting and tracking killing activity on leukemia cells in vivo, which can be used for reference in further clinical trials.

6. Therapeutic Effect on Primary Lymphoma Cells from Lymphoma Patients

Figure 19:
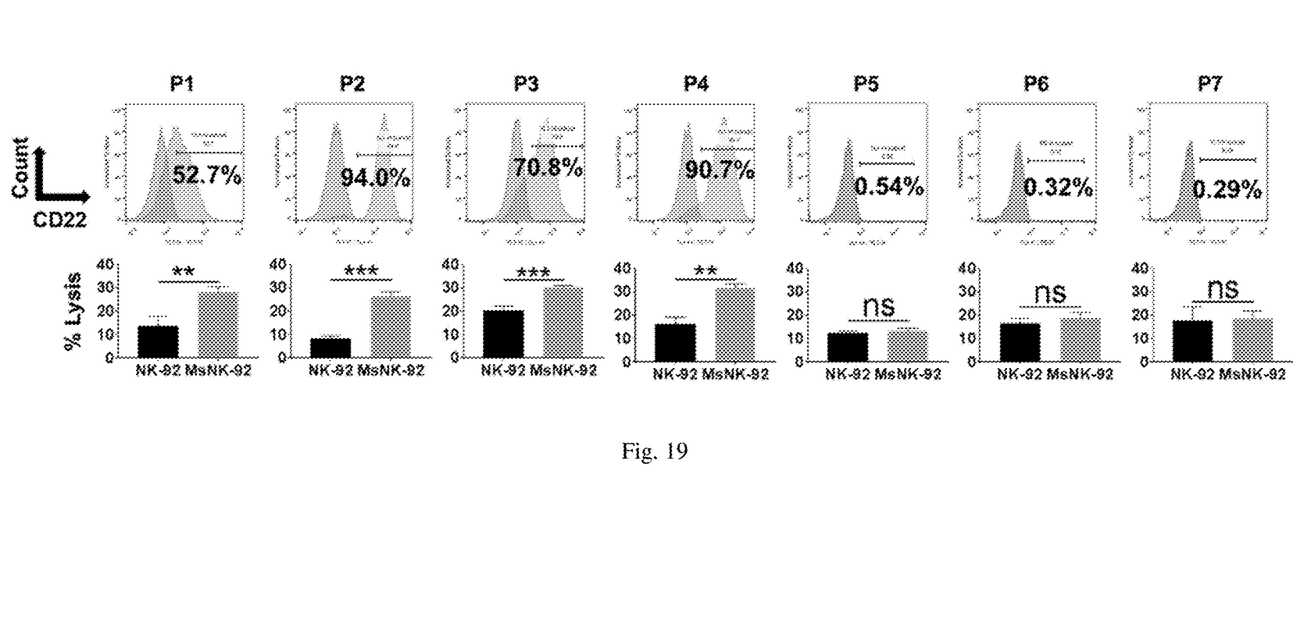
FIG. 19 illustrates NK-92 cells selectively killing CD22 high patient-derived leukemic cells in embodiment 5 of the present disclosure.

To establish the potential translatability of the glyco-engineering strategy, primary lymphoma cells were obtained from lymphoma patients and incubated with glyco-engineered NK-92 cells (FIG. 19). For patient derived lymphoma cells expressing high levels of CD22 (P1-P4 in FIG. 19), significantly enhanced cytotoxicities by glycoengineered NK-92 were observed compared to unmodified NK-92. For patient cells with low levels of CD22 expression (P5-P7), there were no significant changes in cell death when incubated with glycoengineered NK-92 or unmodified NK-92. These results suggested glyco-engineering of NK-92 cells with MPB-sia can be a promising strategy to treat patients with CD22 positive B cell lymphoma.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

What is claimed is:

1. A method for preparing immune cells modified by carbohydrate derivatives, comprising:
    absorbing the carbohydrate derivatives by the immune cells;
    metabolizing the carbohydrate derivatives to form CD22 ligand on a surface of a cell membrane of the immune cells;
    helping the immune cells to identify and target CD22-positive tumor cells; and
    killing the CD22-positive tumor cells, wherein:
        structures of the carbohydrate derivatives are as follows:

a structure of R is at least one of:

2. The method of claim 1, wherein the immune cells comprise at least one of T cells, NK cells, macrophages, DC cells, B cells, or granulocytes.

3. A method for modifying surfaces of immune cells by carbohydrate derivatives, comprising:
    co-culturing the immune cells with the carbohydrate derivatives;
    metabolizing the carbohydrate derivatives by the immune cells; and
    modifying the surfaces of the immune cells by the carbohydrate derivatives, wherein structures of the carbohydrate derivatives are as follows:

a structure of R is at least one of:

4. The method of claim 3, wherein the immune cells comprise at least one of T cells, NK cells, macrophages, DC cells, B cells, or granulocytes.

* * * * *